United States Patent [19]

Anglin et al.

[11] 4,343,746

[45] Aug. 10, 1982

[54] QUATERNARY AMMONIUM THIOMOLYBDATES

[75] Inventors: James R. Anglin, Gibsonia; Yumi P. Ryu, Murrysville; Gary M. Singerman, Monroeville, all of Pa.

[73] Assignee: Gulf Research & Development Company, Pittsburgh, Pa.

[21] Appl. No.: 214,972

[22] Filed: Dec. 10, 1980

[51] Int. Cl.$^3$ .............................................. C07F 11/00
[52] U.S. Cl. ................................................. 260/429 R
[58] Field of Search .................................... 260/429 R

[56] References Cited

U.S. PATENT DOCUMENTS 2,909,541 10/1959 Hugel ............................... 260/429 R
3,539,605 11/1970 Oberhofer ................... 260/429 R X
4,164,473 8/1979 Coupland et al. ............... 260/429 R
4,266,945 5/1981 Karn .................................. 260/429 R Primary Examiner—Helen M. S. Sneed
Attorney, Agent, or Firm—Deane E. Keith; Forrest D. Stine; Donald L. Rose

[57] ABSTRACT

Novel quaternary ammonium thiomolybdates are prepared by contacting an aqueous solution of a thiomolybdate salt with a solution of a water-insoluble quaternary ammonium salt in a water-immiscible organic solvent. For example, mixing a solution of dicocodimethylammonium chloride in toluene with an aqueous solution of potassium thiomolybdate results in a toluene solution containing dicocodimethylammonium thiomolybdate. These quaternary ammonium thiomolybdates find use as additives in motor oils and greases to enhance their antifriction characteristics.

11 Claims, No Drawings

QUATERNARY AMMONIUM THIOMOLYBDATES

SUMMARY OF THE INVENTION

This invention relates to certain novel quaternary ammonium thiomolybdates, which are prepared by the reaction of water-insoluble quaternary ammonium salts and water-soluble thiomolybdate salts. The water-insoluble quaternary ammonium salt is dissolved in a water-immiscible organic solvent, such as benzene or toluene, and agitated with an aqueous solution of a thiomolybdate salt. The resulting quaternary ammonium thiomolybdate is recovered from the organic solvent.

DETAILED DESCRIPTION OF THE INVENTION

The preparation of thiomolybdates of certain nitrogen bases in an aqueous solution is described in U.S. Pat. No. 2,909,541 by a process in which the nitrogen base and sodium thiomolybdate are reacted in the aqueous solution. However, we have found that certain tetrahydrocarbyl-substituted) quaternary ammonium salts are not water-soluble and therefore cannot be effectively reacted in an aqueous solution. According to our invention we have discovered that a water-insoluble quaternary ammonium salt can be reacted with a water-soluble thiomolybdate salt in a two-phase system to produce a group of novel quaternary ammonium thiomolybdates. In this reaction system the water-insoluble quaternary ammonium salt is dissolved in a suitable water-immiscible organic solvent and this solution is contacted and reacted with an aqueous solution of a suitable thiomolybdate salt. In this two-phase reaction system the novel quaternary ammonium thiomolybdate reaction product is in the organic solution while the by-product salt is in the aqueous solution.

The novel compounds of our invention are tetra(alkyl-, alkenyl-)ammonium thiomolybdates as defined by the following formula:

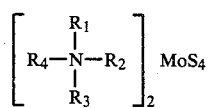

(1)

where $R_1$ is selected from alkyl and alkenyl having from 1 to about 30 carbon atoms, preferably 1 to about 20 carbon atoms, $R_2$ and $R_3$ are independently selected from alkyl and alkenyl having from about 8 to about 30 carbon atoms, preferably from about 12 to about 20 carbon atoms, $R_4$ is selected from alkyl or alkenyl having from 1 to about 20 carbon atoms, preferably 1 to about 4 carbon atoms, and the total number of carbon atoms in $R_1$, $R_2$, $R_3$ and $R_4$ is at least about 25 and the total is no greater than about 80, preferably no greater than about 60 carbon atoms.

The following are typical examples of quaternary ammonium thiomolybdates which can be prepared by the process described herein and which are defined by the above formula:

trioctylmethylammonium thiomolybdate,
dilauryldimethylammonium thiomolybdate,
dicocodimethylammonium thiomolybdate,
dialkyl($C_{12}$ to $C_{16}$)dimethyl ammonium thiomolybdate,
tetradodecylammonium thiomolybdate,
ditallowdimethylammonium thiomolybdate,
bis(hydrogenated tallow)dimethylammonium thiomolybdate,
distearyldimethylammonium thiomolybdate,
tris(hydrogenated tallow)methylammonium thiomolybdate,
dioctadecyldimethylammonium thiomolybdate and
disoyadimethylammonium thiomolybdate.

Mixtures of quaternary ammonium thiomolybdates having different alkyl and/or alkenyl groups and defined by the above formula are also included herein whether prepared by mixing together two or more different quaternary ammonium thiomolybdates or prepared from a mixture of different quaternary ammonium salts. Quaternary ammonium salts containing a mixture of alkyl and alkenyl groups of different carbon numbers can be derived from a mixture of naturally occurring fatty acids. Therefore, the number of carbon atoms for the R groups in the above formula refers to the average number of carbon atoms when a mixture of quaternary ammonium thiomolybdates is involved.

The water-soluble thiomolybdate salts which are used in our process include the alkali metal thiomolybdates such as lithium thiomolybdate, sodium thiomolybdate, potassium thiomolybdate, rubidium thiomolybdate and cesium thiomolybdate. Other water-soluble thiomolybdates are also useful including ammonium thiomolybdate, thallium thiomolybdate and the like. These thiomolybdate salts, which are essentially insoluble in the organic solvents used herein, can be prepared by treating an aqueous alkaline solution of the corresponding molybdate salt with hydrogen sulfide. For example, potassium thiomolybdate is prepared by introducing hydrogen sulfide into an aqueous solution of potassium molybdate and potassium hydroxide.

The water-insoluble quaternary ammonium salts which are reacted as an organic solution with the aqueous solution of the thiomolybdate salt in the two-phase reaction to make the quaternary ammonium thiomolybdates of formula (1) are defined by the following formula:

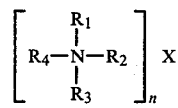

(2)

where $R_1$, $R_2$, $R_3$ and $R_4$ are as defined under formula (1), n is the valence of X and X is selected from chloride, bromide, iodide, sulfate, hydrogen sulfate, lower alkyl sulfate, and the like.

As stated, the water-insoluble quaternary ammonium salt is dissolved in a suitable water-immiscible organic solvent for reaction with a thiomolybdate salt in aqueous solution. Suitable organic solvents include aliphatic hydrocarbons having from about five to about 20 carbon atoms, preferably about five to about ten carbon atoms, such as pentane, hexane, heptane, decane, hexadecane, and the like; aromatic hydrocarbons and halogenated aromatic hydrocarbons having from six to about eight carbon atoms, such as benzene, toluene, xylene, ethylbenzene, chlorobenzene, dichlorobenzene, benzyl chloride, and the like; halogenated aliphatic hydrocarbons having from one to about two carbon atoms, such as methylene chloride, chloroform, carbon tetrachloride, ethylene dichloride, ethylidene chloride, and the like. The suitable organic solvents also include the alkyl esters of aliphatic carboxylic acids having from about four to about seven carbon atoms, including ethyl acetate, butyl acetate, amyl acetate, methyl propionate, and the like; aliphatic ketones having from about five to about ten carbon atoms including isobutylmethyl ketone, diisobutyl ketone, and the like; and alkyl ethers having from about four to about eight carbon atoms such as diethyl ether, ethylpropyl ether, diisopropyl ether, and the like. Mixtures of the above organic solvents can also be used.

The initial concentration of the quaternary ammonium salt in the organic solvent prior to the reaction can broadly range from about one to about 30 weight percent, but preferably it will range from about five to about 20 weight percent. The initial concentration of the thiomolybdate salt in the aqueous solution can be between about one and about 30 weight percent, but the reaction is preferably conducted at a concentration between about three and about 20 weight percent.

The reaction is carried out by contacting the organic solution of the quaternary ammonium salt with the aqueous solution of the thiomolybdate salt. Since temperature is not a critical factor in this reaction, it is convenient to carry out the reaction at about room temperature (20°-25° C.). Although we have not studied the precise mechanism for this two-phase reaction, we believe that the desired reaction takes place at the interface between the organic phase and the aqueous phase. We find that stirring the reactant mixture, preferably with sufficient agitation to cause a substantial increase in the area of contact between the two phases, facilitates the reaction.

At the completion of the reaction the desired water-insoluble tetra(alkyl, alkenyl-)ammonium thiomolybdate is in the organic solution and the by-product salt, such as potassium or sodium chloride, is in the aqueous solution. This thiomolybdate reaction product is recovered by separating the two liquid phases, such as by decantation, and evaporating or distilling off the organic solvent. The resulting dark red thiomolybdate reaction product is a waxy, semi-solid to solid material. This two-phase reaction system conveniently avoids the incorporation of difficult-to-remove water and by-product salt into this waxy, semi-solid or solid product.

The relatively pure tetra(alkyl-, alkenyl-) ammonium thiomolybdate is stable up to a temperature of about 170° to about 200° C. depending on the specific compound. It is preferred to carry out the reaction using quantities ranging from a stoichiometric quantity, that is a ratio of two mols of the quaternary ammonium salt for each mol of the thiomolybdate salt, to a slight stoichiometric excess such as a five to ten percent excess of the thiomolybdate salt. When the reaction is carried out in this range, two desirable objectives are accomplished. First, the most efficient utilization of reactants is accomplished. And second, the quaternary ammonium salt in the organic phase is fully reacted thereby eliminating it as a potential impurity in the quaternary ammonium thiomolybdate product.

The naturally occurring fatty acids are an excellent and convenient source of the higher molecular weight alkyl and alkenyl groups in the quaternary ammonium salt used herein. As used herein, the term alkenyl includes mono-, di- and tri-olefinic groups. These fatty acids can be converted to the corresponding alkenyl group and saturated, if desired, by conventional hydrogenation procedures. For example, oleic acid can be converted to octadecenyl and this can be hydrogenated to octadecyl. Since the naturally occurring fats comprise mixtures of two and generally more carbon chains of different lengths, the resulting quaternary compounds contain the alkenyl and alkyl groups in the same relative proportion as the precursor acids occur in the fat. The relative proportion of alkyl and alkenyl groups of various chain lengths that are derived from different natural sources referred to herein is set out in the following table in which coco is derived from coconut oil, tallow and stearyl are derived from beef fat and soya is derived from soya bean oil.

TABLE

| chain length | coco | tallow | stearyl | soya |
|---|---|---|---|---|
| $C_8$ | 5 | — | — | — |
| $C_{10}$ | 8 | — | — | — |
| $C_{12}$ | 50 | — | — | — |
| $C_{14}$ | 18 | 5 | — | — |
| $C_{16}$ | 8 | 30 | 8 | 15 |
| $C_{17}$ | — | — | 1 | — |
| $C_{18}$ | 11 | 65 | 91 | 85 |

DESCRIPTION OF PREFERRED EMBODIMENTS

Example 1

A 360 g quantity of a commercial mixture containing 75 percent dicocodimethylammonium chloride (0.615 mol) and 25 percent isopropanol was dissolved in one liter of toluene and this solution was stirred with an aqueous solution containing 102 g (0.337 mol) of potassium thiomolybdate in one liter of water at room temperature for 30 minutes. After separating out the dark red toluene layer and water washing it, the toluene was removed under reduced pressure. A quantitative yield of semi-solid, dark red dicocodimethylammonium thiomolybdate was obtained. Analysis of the product for thiomolybdate ion by infrared spectroscopy showed 460/cm and by ultraviolet-visible spectroscopy in toluene showed a band at 470 nm. The calculated elemental analysis for dicocodimethylammonium thiomolybdate was N, 2.7%; S, 12.2% and Mo, 9.15%. The actual elemental analysis was N, 2.63%; S, 12.44% and Mo, 9.3%.

Example 2

A solution containing 1.77 g (3 mmol) of distearyldimethylammonium chloride and seven percent isopropanol was dissolved in 30 ml of methylene chloride. This organic solution was mixed with an aqueous solution containing 0.5 g (1.6 mmol) of potassium thiomolybdate in 10 ml of water. After 15 minutes, the stirring was stopped and the solutions were permitted to separate. The bottom methylene chloride solution was separated from the aqueous layer and was dried over anhydrous magnesium sulfate. The methylene chloride was removed under reduced pressure and 0.9 g of dark red, solid distearyldimethylammonium thiomolybdate was obtained.

Example 3

Dioctadecyldimethylammonium thiomolybdate was prepared by mixing 6.31 g (10 mmol) of dioctadecyldimethylammonium chloride in 100 ml of toluene with 1.5 g (5 mmol) of potassium thiomolybdate in 50 ml of water. The resulting dioctadecyldimethylammonium thiomolybdate (3.8 g) was a dark red solid material.

Example 4

A dialkyl($C_{12-16}$)dimethylammonium thiomolybdate was prepared by dissolving a solution containing 4.1 g (9 mmol) of a dialkyl($C_{12-16}$)dimethylammonium chloride and 32 percent isopropanol in 100 ml of toluene. This solution was agitated with a solution containing 1.5 g (5 mmol) of potassium thiomolybdate in 50 ml of water. The resulting dialkyl($C_{12-16}$)dimethylammonium thiomolybdate (4.5 g), dark red in color, was a semi-solid material.

Example 5

Bis(hydrogenated tallow)dimethylammonium thiomolybdate was prepared from 5.1 g (9 mmol) of the corresponding quaternary ammonium chloride and 1.5 g of potassium thiomolybdate using the same solvents in the same quantities as used in Example 4. The resulting thiomolybdate product (5 g) was also a dark red, semi-solid material.

Example 6

Tris(hydrogenated tallow)methylammonium thiomolybdate was prepared by dissolving a solution containing 5.25 g (6 mmol) of tris(hydrogenated tallow)methylammonium chloride and 50 percent isopropanol in 200 ml of toluene. This solution was agitated with a solution containing 1.0 g (3 mmol) of potassium thiomolybdate in 30 ml of water. The resulting tris(hydrogenated tallow)methylammonium thiomolybdate product (5 g) was a dark red, semi-solid material.

Example 7

A solution containing 120 g (0.297 mol) of trioctylmethylammonium chloride in 800 ml of toluene was vigorously stirred for 30 minutes with a solution containing 51 g (0.168 mol) of potassium thiomolybdate in 500 ml of water. Following the reaction the toluene layer was separated and the toluene was removed at reduced pressure. There was a quantitative recovery of the red viscous trioctylmethylammonium thiomolybdate.

Various members of the novel compounds described herein find use as additives in motor oils or greases to enhance the antifriction and EP characteristics. For example, the presence of one percent trioctylmethylammonium thiomolybdate in a diurea-type grease such as described in U.S. Pat. No. 4,065,395 increased the maximum load without seizure, welding or scoring as measured by ASTM D2509 from 30 lb/ft$^2$ without the additive to 60 lb/ft$^2$ with the additive.

It is to be understood that the above disclosure is by way of specific example and that numerous modifications and variations are available to those of ordinary skill in the art without departing from the true spirit and scope of the invention.

We claim:
1. The quaternary ammonium thiomolybdate having the formula

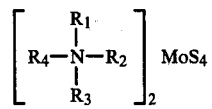

wherein $R_1$ is alkyl or alkenyl having from one to about 30 carbon atoms; $R_2$ and $R_3$ are independently selected from alkyl and alkenyl having from about 8 to about 30 carbon atoms; $R_4$ is alkyl or alkenyl having from one to about 20 carbon atoms and the total number of carbon atoms in $R_1$, $R_2$, $R_3$ and $R_4$ is between about 25 and about 80.

2. The quaternary ammonium thiomolybdate in accordance with claim 1 wherein $R_1$ has from one to about 20 carbon atoms, $R_2$ and $R_3$ have from about 12 to about 20 carbon atoms, $R_4$ has from one to about 4 carbon atoms, and the total number of carbon atoms in $R_1$, $R_2$, $R_3$ and $R_4$ is between about 25 and about 60.

3. The quaternary ammonium thiomolybdate in accordance with claim 2 wherein $R_1$ and $R_4$ are methyl.

4. The quaternary ammonium thiomolybdate in accordance with claim 3 wherein $R_2$ and $R_3$ are coco.

5. The quaternary ammonium thiomolybdate in accordance with claim 3 wherein $R_2$ and $R_3$ are stearyl.

6. The quaternary ammonium thiomolybdate in accordance with claim 3 wherein $R_2$ and $R_3$ are octadecyl.

7. The quaternary ammonium thiomolybdate in accordance with claim 3 wherein $R_2$ and $R_3$ are hydrogenated tallow.

8. The quaternary ammonium thiomolybdate in accordance with claim 1 wherein $R_1$, $R_2$ and $R_3$ have from about 8 to about 20 carbon atoms and $R_4$ is methyl.

9. The quaternary ammonium thiomolybdate in accordance with claim 8 wherein $R_1$, $R_2$ and $R_3$ are octyl.

10. The quaternary ammonium thiomolybdate in accordance with claim 2 wherein $R_1$, $R_2$ and $R_3$ have from about 12 to about 20 carbon atoms and $R_4$ is methyl.

11. The quaternary ammonium thiomolybdate in accordance with claim 10 wherein $R_1$, $R_2$ and $R_3$ are hydrogenated tallow.

* * * * *